US012667666B2

(12) United States Patent     (10) Patent No.:    US 12,667,666 B2

Ulrich et al.     (45) Date of Patent:     Jun. 30, 2026

(54) SYSTEM AND METHOD OF MODIFYING USER PROFILE IN AUTOMATED INSULIN DELIVERY

(71) Applicant: Tandem Diabetes Care, Inc., San Diego, CA (US)

(72) Inventors: Thomas R. Ulrich, Oceanside, CA (US); Shaun Buchanan, Hampstead, NC (US)

(73) Assignee: Tandem Diabetes Care, Inc., San Diego, CA (US)

( * ) Notice: Subject to any disclaimer, the term of this patent is extended or adjusted under 35 U.S.C. 154(b) by 723 days.

(21) Appl. No.: 18/071,814

(22) Filed: Nov. 30, 2022

(65) Prior Publication Data

US 2023/0166037 A1    Jun. 1, 2023

Related U.S. Application Data

(60) Provisional application No. 63/284,299, filed on Nov. 30, 2021.

(51) Int. Cl.
*A61M 5/172*       (2006.01)
*A61M 5/142*       (2006.01)

(52) U.S. Cl.
CPC ...... *A61M 5/1723* (2013.01); *A61M 5/14244* (2013.01); *A61M 2202/0486* (2013.01); *A61M 2205/502* (2013.01)

(58) Field of Classification Search
CPC ............ A61M 5/1723; A61M 5/14244; A61M 2202/0486; A61M 2205/502; A61M 2005/14208
See application file for complete search history.

(56) References Cited

U.S. PATENT DOCUMENTS

| | | | |
|---|---|---|---|
| 2,454,929 | A | 11/1948 | Kempton |
| 2,728,355 | A | 12/1955 | Dahl |
| 2,989,086 | A | 6/1961 | Dahl |
| 4,529,401 | A | 7/1985 | Leslie et al. |
| 4,776,842 | A | 10/1988 | Franetzki et al. |
| 4,869,431 | A | 9/1989 | Jubert et al. |

(Continued)

FOREIGN PATENT DOCUMENTS

| | | |
|---|---|---|
| KR | 10-2019-0013922 A | 2/2019 |
| KR | 10-2019-0051899 A | 5/2019 |
| WO | 2021-0113859 A1 | 6/2021 |

OTHER PUBLICATIONS

Liu, et al., "Cilostazol attenuates the severity of perifpheral arterial occlusive disease in patients with type 2 diabetes: the role of plasma soluble receptor for advanced glycation end-products", Endocrine (2015), Human Press, Inc., 49:703-710.

(Continued)

*Primary Examiner* — Jason E Flick

(74) *Attorney, Agent, or Firm* — Merchant & Gould P.C.

(57) ABSTRACT

Disclosed herein are systems and methods for automated insulin delivery that provide for adaptive closed loop control that can modify the stored basal profile used by the closed loop algorithm to better reflect the user's actual needs. Actual delivery rates calculated by the closed loop algorithm can be compared to the user's stored profile. If the differences between the actual delivery rates and the stored profile are statistically significant, the stored profile can be modified.

16 Claims, 8 Drawing Sheets

(56) References Cited

U.S. PATENT DOCUMENTS

| | | |
|---|---|---|
| 4,931,050 A | 6/1990 | Idriss |
| 5,078,683 A | 1/1992 | Sancoff et al. |
| 5,131,816 A | 7/1992 | Brown et al. |
| 5,356,379 A | 10/1994 | Vaillancourt |
| 5,429,602 A | 7/1995 | Hauser |
| 5,482,446 A | 1/1996 | Williamson et al. |
| 5,522,798 A | 6/1996 | Johnson et al. |
| 5,718,562 A | 2/1998 | Lawless et al. |
| 6,186,982 B1 | 2/2001 | Gross et al. |
| 6,346,095 B1 | 2/2002 | Gross et al. |
| 6,530,900 B1 | 3/2003 | Daily et al. |
| 6,544,229 B1 | 4/2003 | Danby et al. |
| 6,582,393 B2 | 6/2003 | Sage, Jr. |
| 6,589,229 B1 | 7/2003 | Connelly et al. |
| 6,767,188 B2 | 7/2004 | Vrane et al. |
| 7,268,859 B2 | 9/2007 | Sage, Jr. et al. |
| 7,879,026 B2 | 2/2011 | Estes et al. |
| 7,931,642 B2 | 4/2011 | Tonnies |
| 7,967,773 B2 | 6/2011 | Amborn et al. |
| 8,409,133 B2 | 4/2013 | Pesach et al. |
| 8,552,880 B2 | 10/2013 | Kopp et al. |
| 8,936,573 B2 | 1/2015 | Blomquist |
| 9,056,167 B2 | 6/2015 | Pesach et al. |
| 9,433,733 B2 | 9/2016 | Moberg et al. |
| 9,440,025 B2 | 9/2016 | Kanderian, Jr. et al. |
| 9,486,171 B2 | 11/2016 | Saint |
| 9,486,571 B2 | 11/2016 | Rosinko |
| 9,579,452 B2 | 2/2017 | Adair et al. |
| 9,669,160 B2 | 6/2017 | Harris et al. |
| 9,833,177 B2 | 12/2017 | Blomquist |
| 9,867,937 B2 | 1/2018 | Saint et al. |
| 9,867,953 B2 | 1/2018 | Rosinko |
| 10,016,561 B2 | 7/2018 | Saint et al. |
| 10,049,768 B2 | 8/2018 | Blomquist |
| 10,052,049 B2 | 8/2018 | Blomquist et al. |
| 10,493,202 B2 | 12/2019 | Hayter |
| 10,569,016 B2 | 2/2020 | Rosinko |
| 10,726,100 B2 | 7/2020 | Blomquist et al. |
| 10,926,025 B2 | 2/2021 | Betts et al. |
| 10,943,687 B2 | 3/2021 | Blomquist |
| 10,991,456 B2 | 4/2021 | Hayter et al. |
| 11,083,843 B2 | 8/2021 | Hayter et al. |
| 11,090,432 B2 | 8/2021 | DeBelser et al. |
| 11,116,901 B2 | 9/2021 | Harris |
| 11,185,632 B2 | 11/2021 | Budiman et al. |
| 11,217,339 B2 | 1/2022 | Blomquist |
| 11,224,693 B2 | 1/2022 | Ulrich et al. |
| 11,291,763 B2 | 4/2022 | Blomquist et al. |
| 11,464,908 B2 | 10/2022 | Michaud et al. |
| 11,471,598 B2 | 10/2022 | Estes |
| 11,607,492 B2 | 3/2023 | Rosinko et al. |
| 11,654,236 B2 | 5/2023 | Kearns et al. |
| 11,676,694 B2 | 6/2023 | Kruse et al. |
| 11,694,794 B2 | 7/2023 | Farnan et al. |
| 2008/0172027 A1 | 7/2008 | Blomquist |
| 2008/0172030 A1 | 7/2008 | Blomquist |
| 2010/0121274 A1 | 5/2010 | Oh et al. |
| 2013/0046281 A1 | 2/2013 | Javitt |
| 2019/0125969 A1 | 5/2019 | Montgomery et al. |
| 2019/0321551 A1 | 10/2019 | Parikh et al. |
| 2020/0368430 A1 | 11/2020 | Ulrich et al. |
| 2021/0001044 A1 | 1/2021 | Michaud et al. |
| 2021/0016005 A1* | 1/2021 | Raskin .................. G16H 10/40 |
| 2021/0030955 A1 | 2/2021 | Desborough et al. |
| 2021/0085869 A1 | 3/2021 | El-Khatib et al. |
| 2021/0113766 A1 | 4/2021 | Kearns et al. |
| 2021/0353857 A1 | 11/2021 | Ulrich et al. |
| 2022/0062553 A1 | 3/2022 | Constantin et al. |
| 2022/0233772 A1 | 7/2022 | Ulrich et al. |
| 2022/0233773 A1 | 7/2022 | Rueda et al. |
| 2022/0265927 A1 | 8/2022 | Harris et al. |
| 2023/0034408 A1 | 2/2023 | Nichols et al. |
| 2023/0037465 A1 | 2/2023 | Rueda et al. |
| 2023/0040677 A1 | 2/2023 | Tran et al. |
| 2023/0113755 A1 | 4/2023 | Lu et al. |

OTHER PUBLICATIONS

Extended European Search Report, EP22902108.4 issued Oct. 10, 2025, 10 pages.
Notice of Transmittal of the International Search Report and The Written Opinion of the International Searching Authority, PCT/US2022/051344, issued Apr. 17, 2023, 11 pages.

* cited by examiner

SYSTEM AND METHOD OF MODIFYING USER PROFILE IN AUTOMATED INSULIN DELIVERY

RELATED APPLICATION

The present application claims the benefit of U.S. Provisional Application No. 63/284,299, filed Nov. 30, 2021, which is hereby incorporated herein in its entirety by reference.

TECHNICAL FIELD

The present disclosure relates generally to ambulatory infusion pumps and, more particularly, to operation of ambulatory infusion pumps in a closed-loop or semi-closed-loop fashion.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices that can provide continuous subcutaneous insulin injection and/or infusion therapy as an alternative to multiple daily insulin injections via syringe or injector pen. Such ambulatory infusion pumps may be worn by the user, may use replaceable medicament cartridges, and may deliver other medicaments alone, or in combination with insulin. Such medicaments include glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as continuous glucose monitoring (CGM) devices. Most CGM devices consist of a sensor placed under the patient's skin and affixed to the patient via an adhesive patch, a transmitter, and a monitor. Such a CGM device samples the patient's interstitial fluid periodically (e.g., once every 1-5 minutes) to estimate blood glucose levels over time. CGMs are advantageous because they provide more frequent insights into a user's blood glucose levels yet do not require a finger stick each time a reading is taken.

Ambulatory infusion pumps may incorporate a CGM within the hardware of the pump or may communicate with a dedicated CGM directly via a wired connection or indirectly via a wireless connection using wireless data communication protocols to communicate with a separate device (e.g., a dedicated remote device or a smartphone). One example of integration of ambulatory infusion pumps with CGM devices is described in U.S. Patent Publication No. 2014/0276419, which is hereby incorporated by reference herein. Ambulatory infusion pumps typically allow the user or caregiver to adjust the amount of insulin or other medicament delivered by a basal rate or a bolus, based on blood glucose data obtained by a CGM device, and in some cases include the capability to automatically adjust such medicament delivery. For example, based on CGM readings, some ambulatory infusion pumps may automatically adjust or prompt the user to adjust the level of medicament being administered or planned for administration or, in cases of abnormally low blood glucose readings, reducing or temporarily ceasing insulin administration.

In some cases, ambulatory insulin pumps may be configured to deliver insulin based on CGM data in a closed-loop or semi-closed-loop fashion. Some systems including these features may be referred to as automated insulin delivery (AID) systems or artificial pancreas systems because these systems serve to mimic biological functions of the pancreas for persons with diabetes.

SUMMARY

Disclosed herein are systems and methods for automated insulin delivery that provide for adaptive closed loop control that can modify the stored basal profile used by the closed loop algorithm to better reflect the user's actual needs. Actual delivery rates calculated by the closed loop algorithm can be compared to the user's stored profile. If the differences between the actual delivery rates and the stored profile are statistically significant, the stored profile can be modified.

In an embodiment, an ambulatory infusion pump system can include a pump mechanism configured to facilitate delivery of insulin to a user, a communications interface adapted to receive glucose levels from a continuous glucose monitor and at least one processor functionally linked to the pump mechanism and the communications device. The at least one processor can be configured to automatically calculate insulin doses with a closed loop delivery algorithm based on glucose levels received from the continuous glucose monitor with the closed loop delivery algorithm employing a default basal profile when the user's glucose levels are within a target glucose level range defining a default basal rate for a plurality of times of day. The closed loop delivery algorithm can be configured to increase or decrease insulin delivery from the default basal rate when the user's glucose levels are outside of the target glucose level range. The processor can further be configured to record actual insulin delivery rates delivered to the user based on the closed loop delivery algorithm for the plurality of times of day and conduct a comparison of the default basal profile with the actual insulin delivery rates to determine whether a difference between the actual insulin delivery rates and the default basal profile is statistically significant. If the difference between the actual insulin delivery rates and the default basal profile is statistically significant, the default basal profile can be modified.

In an embodiment a method of diabetes therapy includes automatically calculating insulin doses with a closed loop delivery algorithm based on glucose levels received from the continuous glucose monitor. The closed loop delivery algorithm can employ a default basal profile when the user's glucose levels are within a target glucose level range, the default basal profile defining a default basal rate for a plurality of times of day and the closed loop delivery algorithm configured to increase or decrease insulin delivery from the default basal rate when a user's glucose levels are outside of the target glucose level range. Insulin can automatically be delivered to the user based on the calculated insulin doses. Actual insulin delivery rates delivered to the user based on the closed loop delivery algorithm can be recorded for the plurality of times of day. The default basal profile can be compared with the actual insulin delivery rates to determine whether a difference between the actual insulin delivery rates and the default basal profile is statistically significant. If the difference between the actual insulin delivery rates and the default basal profile is statistically significant, the default basal profile can be modified.

BRIEF DESCRIPTION OF THE DRAWINGS

The invention may be more completely understood in consideration of the following detailed description of various embodiments of the invention in connection with the accompanying drawings, in which.

Figure 1:
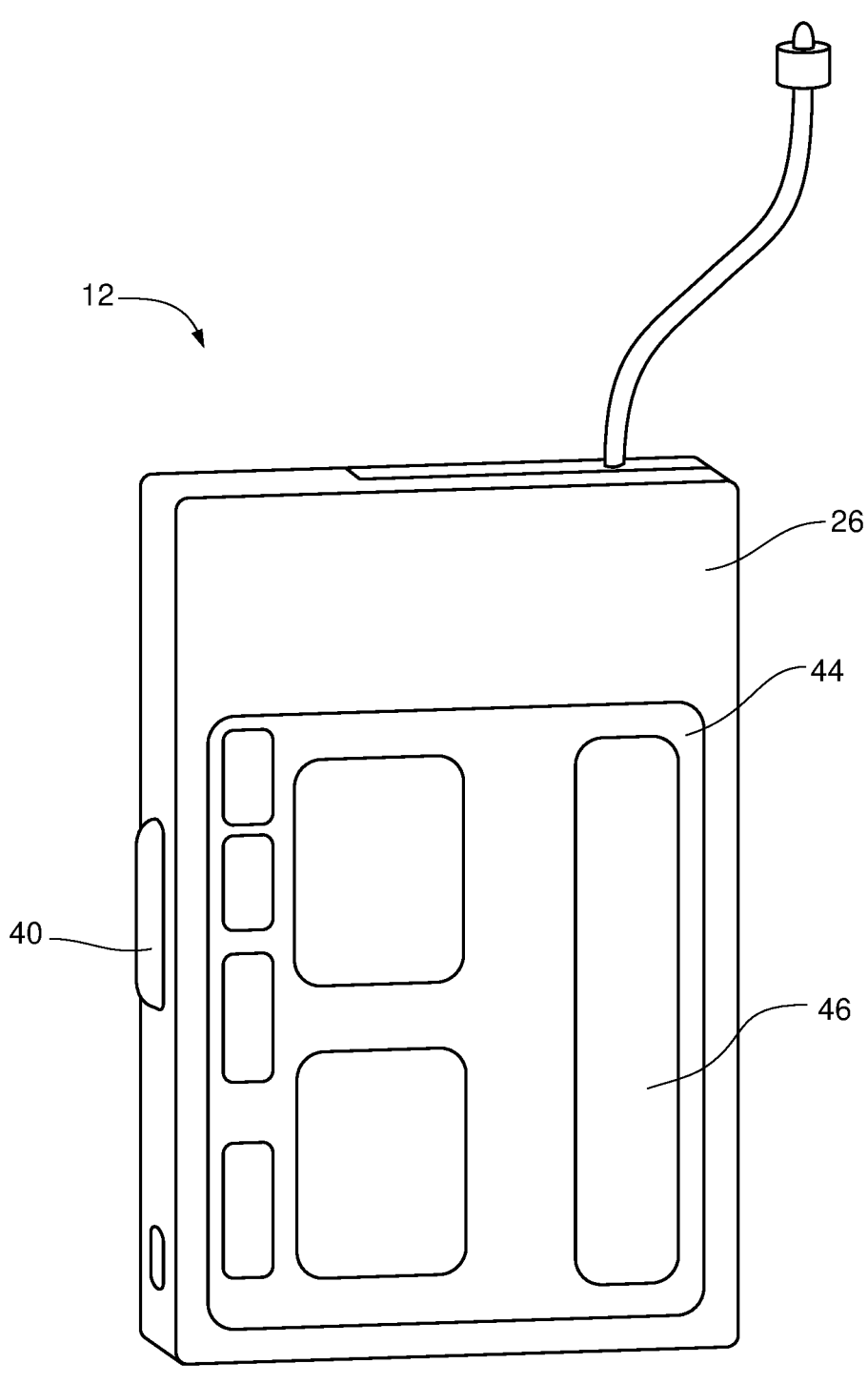
FIG. 1 is an embodiment of an ambulatory infusion pump for use with embodiments of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the disclosure.

FIG. 1 depicts an example infusion pump that can be used in conjunction with one or more embodiments of the ambulatory infusion pump system of the present disclosure. Pump 12 includes a pumping or delivery mechanism and reservoir for delivering insulin or other medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display (e.g., a dedicated remote display or a CGM display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, previously incorporated by reference above. It is to be appreciated that pump 12 may be optionally configured to deliver one or more additional or other medicaments to a patient.

Figure 2:
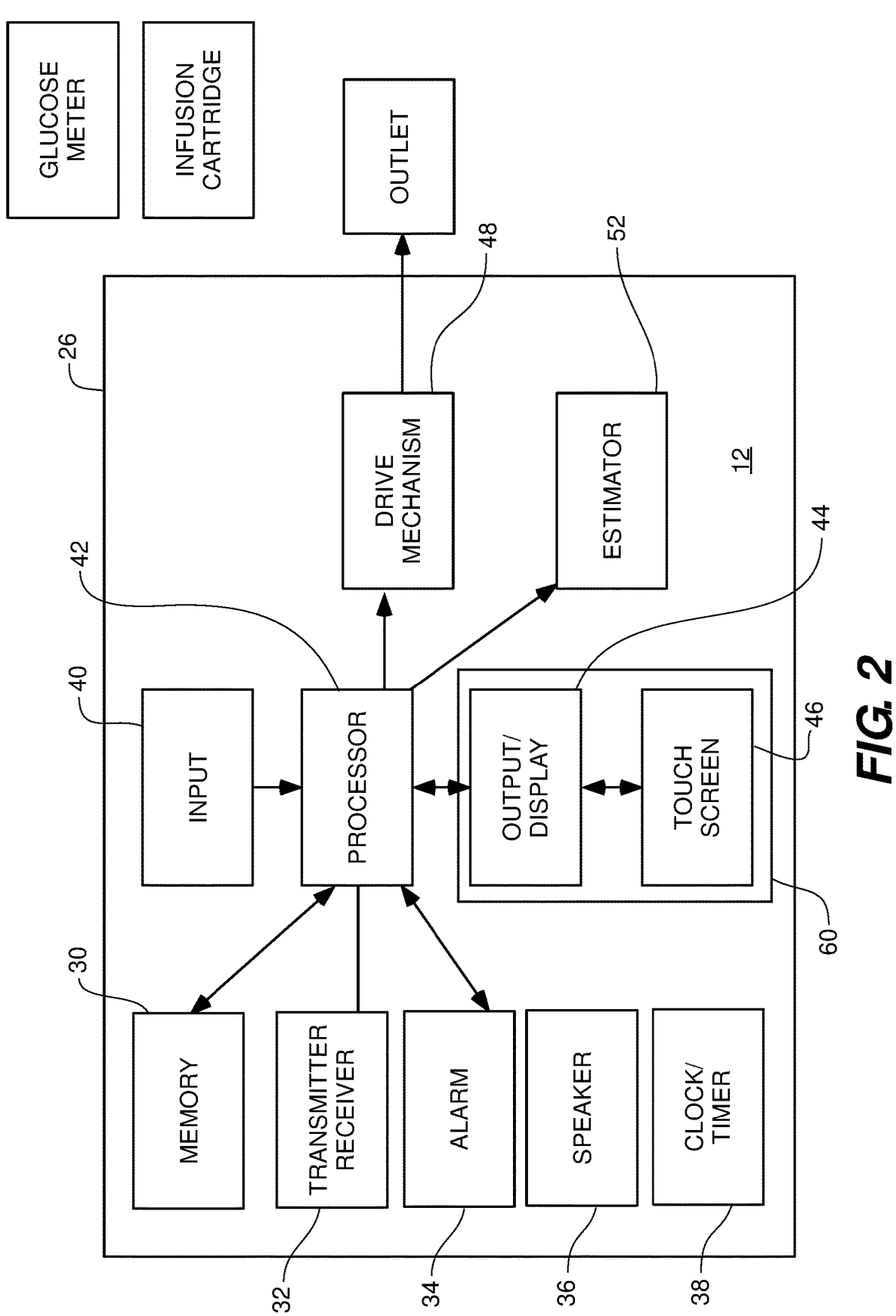
FIG. 2 is a block diagram of the ambulatory infusion pump of FIG. 1.

FIG. 2 illustrates a block diagram of some of the features that may be included within the housing 26 of pump 12. The pump 12 can include a processor 42 that controls the overall functions of the pump. The pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices through the transmitter/receiver 32 such as a remote device (e.g., CGM device), a remote control device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. The processor 42 may also include programming to receive signals and/or other data from an input device, such as, by way of example, a pressure sensor, a temperature sensor, an accelerometer, a GPS receiver or the like.

Figures 3A, 3B:
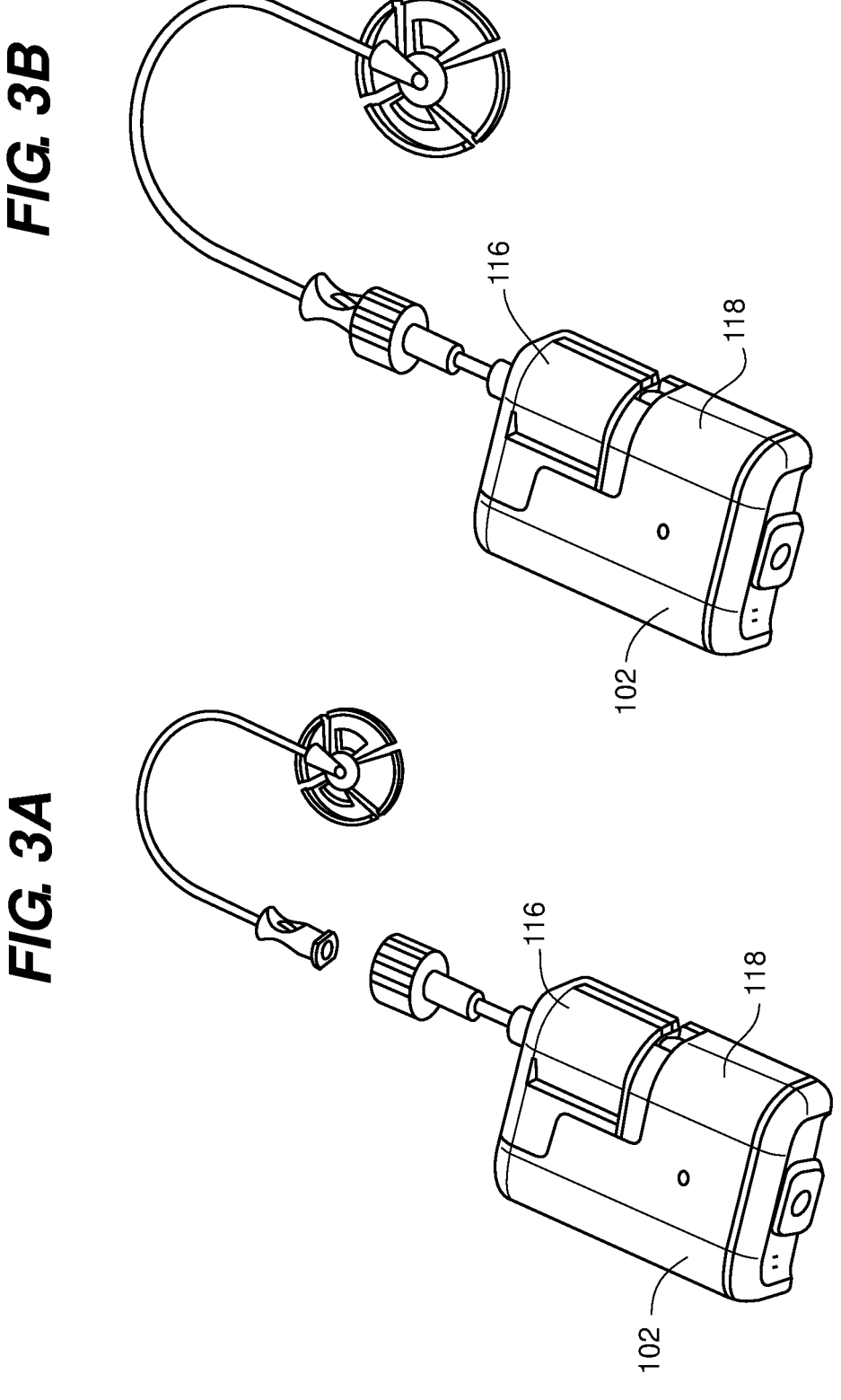
FIGS. 3A-3B are an alternate embodiment of an ambulatory infusion pump for use with embodiments of the disclosure.

FIGS. 3A-3B depicts another infusion pump that can be used in conjunction with one or more embodiments of the ambulatory infusion pump system of the present disclosure. Pump 102 includes a pump drive unit 118 and a medicament cartridge 116. Pump 102 includes a processor that may communicate with one or more processors within the pump 102 and/or one or more processors of other devices such as a remote device (e.g., a CGM device), a remote control device, or a consumer electronic device (e.g., laptop computer, personal computer, tablet computer, smartphone, electronic watch, electronic health or fitness monitor, or personal digital assistant). The processor 42 may also include programming to receive signals and/or other data from an input device, such as, by way of example, a pressure sensor, a temperature sensor, or the like. Pump 102 also includes a processor that controls some or all of the operations of the pump. In some embodiments, pump 102 receive commands from a separate device for control of some or all of the operations of the pump. Such separate device can include, for example, a dedicated remote control device or a consumer electronic device such as a smartphone having a processor executing an application configured to enable the device to transmit operating commands to the processor of pump 102. In some embodiments, processor can also transmit information to one or more separate devices, such as information pertaining to device parameters, alarms, reminders, pump status, etc. Such separate device can include any remote display, remote control device, or a consumer electronic device as described above. Pump 102 can also incorporate any or all of the features described with respect to pump 12 in FIG. 2. In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
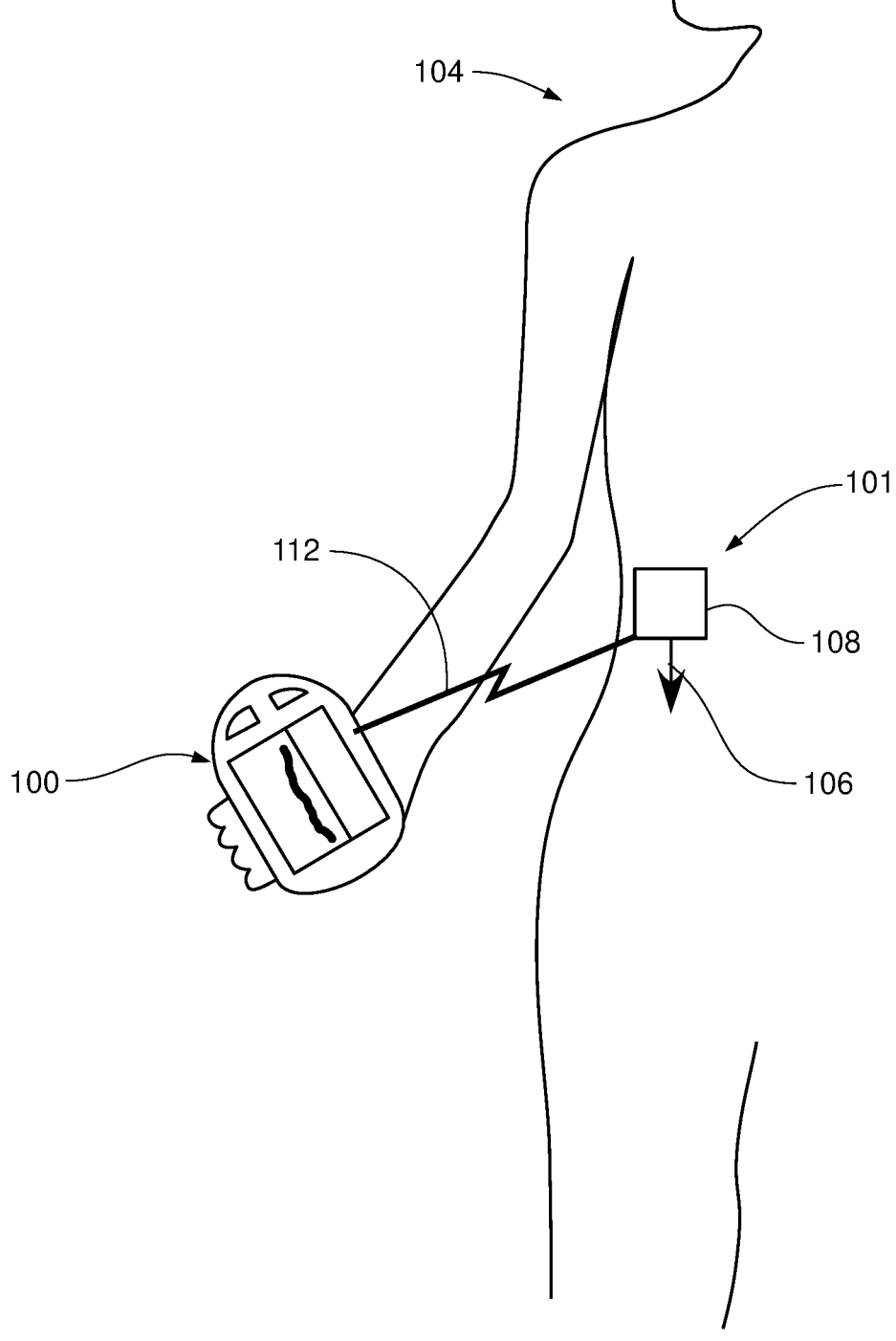
FIG. 4 is an embodiment of a CGM for use with embodiments of the disclosure.

FIG. 4 depicts an example CGM system that can be used in conjunction with one or more embodiments of the ambulatory infusion pump system of the present disclosure. The CGM system includes a sensor 101, a sensor probe 106, a sensor body 108, a receiver, and a monitor (receiver and monitor are depicted as device 100 in FIG. 4). In this embodiment, the sensor 101 is removably affixed to a user 104 and includes a sensor probe 106 configured for trans-cutaneous insertion into the user 104. When placed, the sensor probe 106 reacts with the user's interstitial fluid which produces a signal that can be associated with the user's blood glucose level. The sensor 101 further includes a sensor body 108 that transmits data associated with the signal to the receiver 100 via wired or wireless connection (as represented by arrow line 112). In preferred embodiments, the receiver 100 receives the transmitted data wirelessly by any suitable means of wireless communication. By way of example only, this wireless communication may include a near field communication (NFC) radio frequency (RF) transmitter or a transmitter operating according to a "Wi-Fi" or Bluetooth® protocol, Bluetooth® low energy protocol or the like. Further detail regarding such systems and definitions of related terms can be found in, e.g., U.S. Pat. Nos. 8,311,749, 7,711,402 and 7,497,827, each of which is hereby incorporated by reference in its entirety.

With the infusion pump and CGM interfaced, the CGM can automatically transmit the CGM data to the pump. The pump can then use this data to automatically determine therapy parameters and suggest a therapy adjustment to the user or automatically deliver the therapy adjustment to the user. These therapy parameters including thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

For example, if the CGM readings indicate that the user has or is predicted to have a high blood glucose level, the ambulatory infusion system can automatically calculate an insulin dose sufficient to reduce the user's blood glucose level below a threshold level or to a target level and automatically deliver the dose. Alternatively, the ambulatory infusion system can automatically suggest a change in therapy upon receiving the CGM readings such as an increased insulin basal rate or delivery of a bolus but can require the user to accept the suggested change prior to delivery rather than automatically delivering the therapy adjustments.

By way of further example, if the CGM readings indicate that the user has or is predicted to have a low blood glucose level (hypoglycemia), the ambulatory infusion system can, for example, automatically reduce or suspend a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the patient address the hypoglycemic condition as necessary (e.g., ingest carbohydrates), singly or in any desired combination or sequence.

Figure 5:
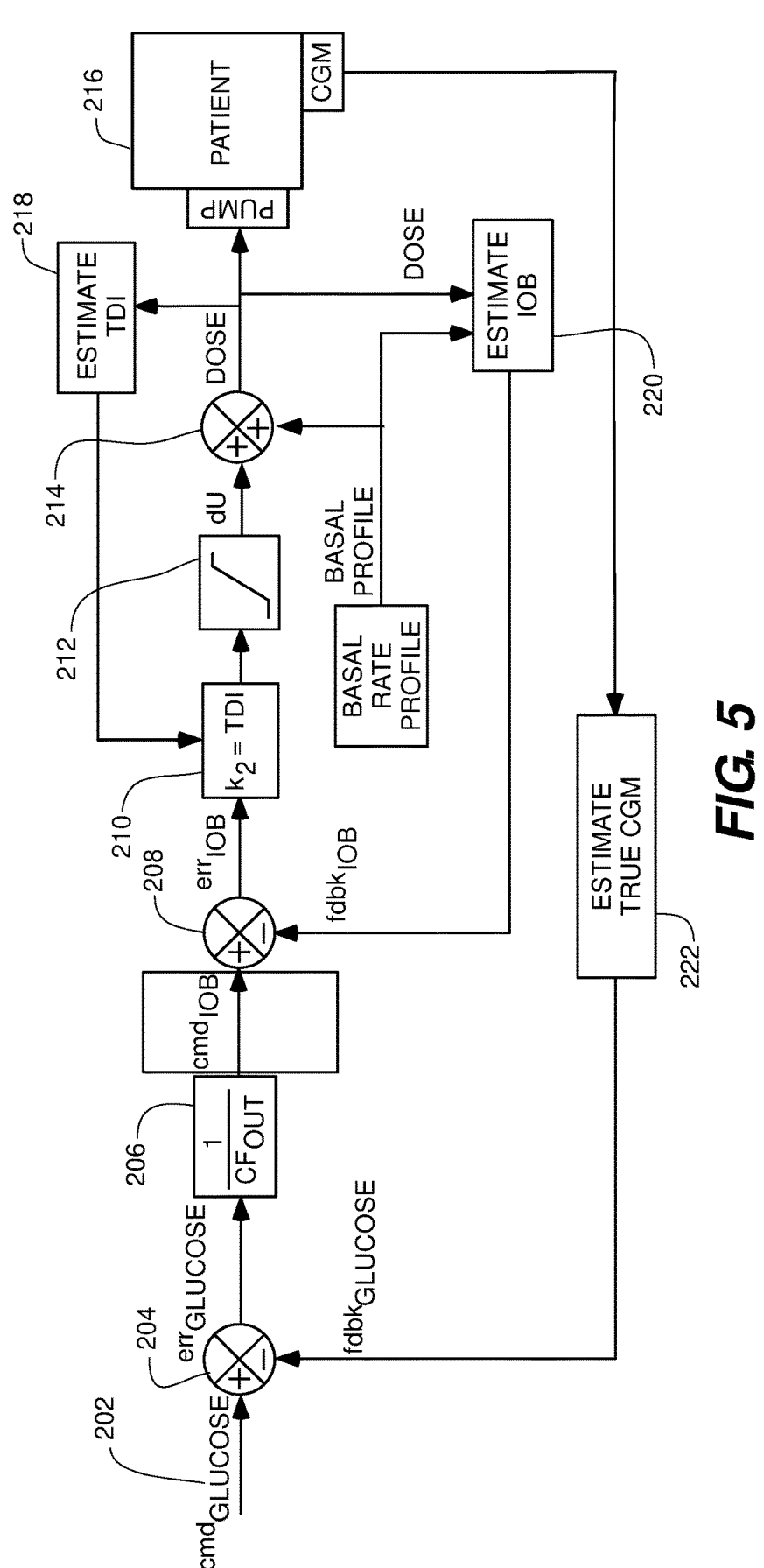
FIG. 5 is a schematic representation of a closed-loop insulin delivery algorithm according to the disclosure.

A schematic representation of a control algorithm for automatically adjusting insulin delivery based on CGM data is depicted in FIG. 5. This figure depicts an algorithm for increasing basal rate that utilizes a cascaded loop. The logic for decreasing basal rate is not depicted. In the depicted embodiment, there is a glucose set-point/command (cmd) that is determined at step 202. The glucose set point is a target value at which the algorithm attempts to maintain a user's blood glucose. This value can vary based on a number of factors, including the user's physiology, whether the user is awake or asleep, how long the user has been awake, etc. The glucose set point is compared to the actual CGM feedback (fdbk) at step 204 to determine a glucose error value (err) that is the difference between the set point and the feedback. In various embodiments, the CGM feedback can be a current glucose level reading received from a CGM or can be a predicted future glucose value based on previous glucose readings. For example, the system may predict a glucose level 30 minutes in the future (Gpred30) and utilize the predicted value as the fdbk glucose value. The errGLU-COSE value at step 206 is multiplied by a constant (1/CF), in which CF is the user's correction factor, or amount by which one unit of insulin lowers the user's blood glucose. This calculation determines how much insulin is needed to correct the glucose error, which is how much insulin on board (IOB) is needed in the user's body. This IOB value then determines an appropriate estimated insulin on board (IOB) set point for the patient.

The estimated IOB level determined at step 206 is then taken as the command (cmdIOB) for the inner loop and based on a difference of an IOB feedback value (fdbkIOB) and the cmdIOB set point at step 208, an IOB error value (errIOB) is determined. At step 210, the errIOB value is multiplied by a constant kl (relating to insulin-dependent glucose uptake in the body) and an estimate of the total daily insulin (TDI) of the user. This adjusts the errIOB to be proportional to the constant and the user's total daily intake of insulin. At step 212, a limiter function is applied to the value calculated at step 210. The limiter function can prevent the calculated amount from being larger or smaller than preset limits. The result is an insulin amount dU, which is the amount by which the user's stored basal rate should be modified. The insulin delivery rate for the user for the next closed loop interval is therefore calculated by modifying the user's stored basal rate profile by the dU value at step 214.

After the dose is calculated, it can be delivered to the user at step 216 and can also be used to update the estimated TDI for the user at step 218. The dose can also be used to update the estimated IOB level for the user at step 220 by comparing the actual insulin delivered to the programmed basal rate. The updated estimated IOB then becomes the new fdbkIOB for the IOB comparison at step 208. When new CGM values are received from the CGM, an estimated true CGM can be determined based on various factors such as, for example, the calibration status of the CGM sensor. The estimated true CGM value then becomes the new fdbkGLU-COSE value for the outer loop comparison with cmdGLU-COSE at step 204 or the estimated true CGM value can be used to update the predicted future glucose level (i.e., Gpred30) for the comparison. The algorithm then proceeds through to calculate a new estimated IOB and to the inner IOB loop for calculation of an insulin dose as described above. In one embodiment, a new CGM value is received every 5 minutes and the algorithm executes as set forth above every 5 minutes.

In some systems, the closed loop algorithm delivers insulin to the user according to the stored basal profile when the user's glucose levels remain within a target range. The general concept behind closed loop algorithms such as the algorithm described above is to use continuous glucose feedback to adjust insulin delivery when the stored baseline basal profile is delivering too much or not enough insulin. If the stored basal profile is outdated and/or the user's needs have changed such that the basal profile inaccurately reflects the user's insulin requirements, the system will be constantly adjusting to attempt to more accurately meet the user's needs and it will be difficult to maintain good glucose level control.

Figure 6B:
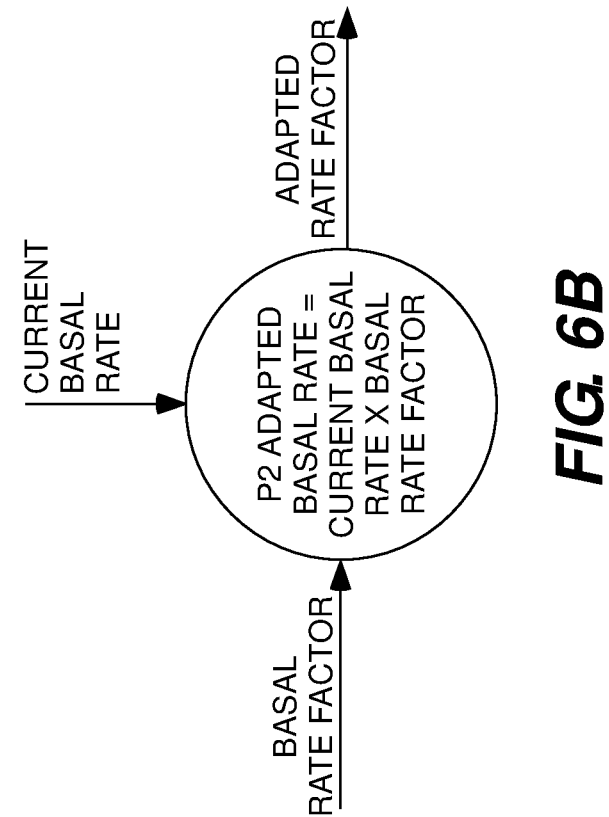
FIGS. 6A-6B depict aspects of a closed-loop insulin delivery algorithm according to the disclosure.
Figure 6A:
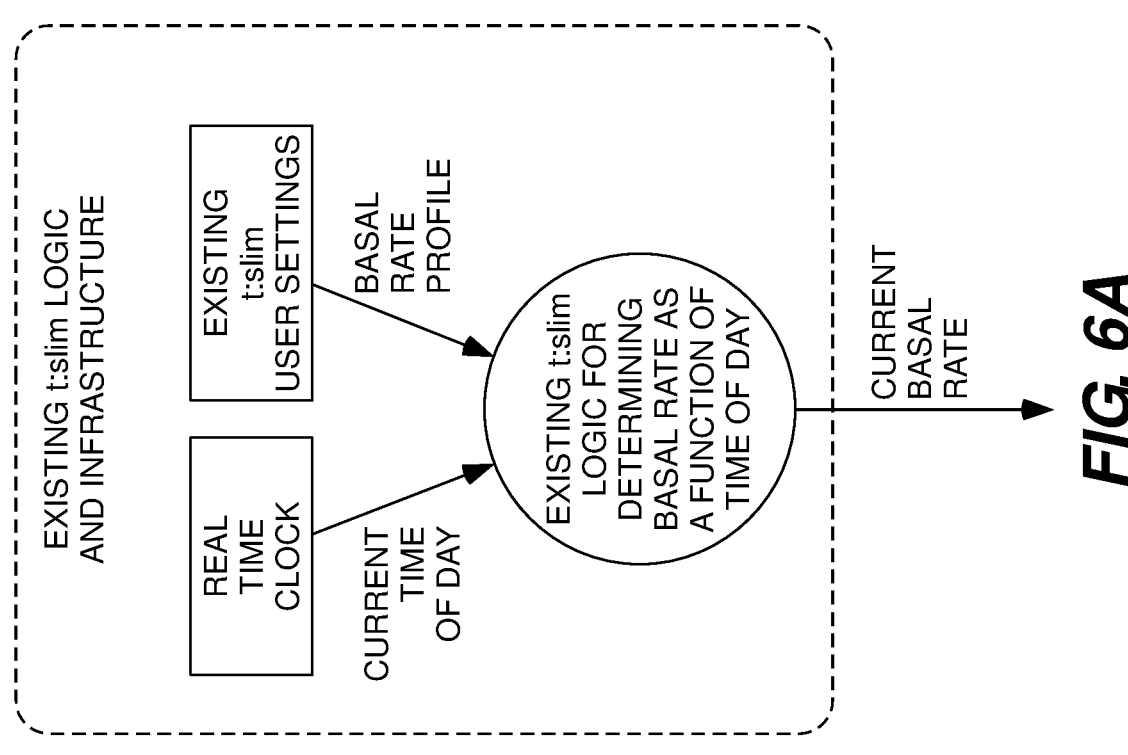

For example, typically insulin pump systems determine basal rate as a time of day. Referring to FIG. 6A, a real time clock is used with stored settings to determine the basal rate to be delivered at a given time of day. FIG. 6B depicts an additional step according to aspects of the disclosure after the determination of the default current basal rate in FIG. 6A. Following the initial determination for a current basal rate, the system can generate a basal rate factor based on the user's glucose levels that is multiplied by the current basal rate to create an adjusted basal rate. However, while the system can therefore modify a current basal rate at a given time based on glucose levels, there may be an issue with the entire basal profile that should be addressed.

For example, the user may have a programmed basal profile as follows: 1 u/hr from 12:00 AM to 6:30 AM, 2 u/hr from 6:30 AM to 8:30 am, 1.2 u/hr from 8:30 AM to 11:50 AM, 2.2 u/hr from 11:50 AM to 1:05 PM, 1 u/hr from 1:05 PM to 5:55 PM, 2 u/hr from 5:55 PM to 7:00 PM and 1 u/hr from 7:00 PM to 12:00 AM. As such, optimizing the overall basal profile is more complicated that simply modifying a given basal rate. Applicant has previously disclosed a system and method in U.S. Provisional Application No. 63/228, 880 entitled Adaptive Control for Automated Insulin Delivery for Diabetes Therapy in which the entire basal profile can be modified using the basal rate factor noted above to change all of the basal rates in the basal profile by a ratio for a period of time. In the present disclosure, Applicant provides a system and method for determining whether the shape of the basal profile is correct, rather than just the magnitude. For example, employing a basal rate factor of 1.25 that increases all basal rates by 25% changes the magnitude of the profile, but does not modify the underlying shape of the profile. The underlying shape of the profile can be modified by individually modifying one or more of the stored rates. Further, in order to optimize the shape of the basal profile, it must be determined if a change to the shape, such as, e.g., increasing the basal rate from 11:50-1:05 above from 2.2 u to 2.5 u, is statistically significant. Similarly, it must be determined how small a change to the shape can be to be statistically significant with the idea that any modification should be made slowly with small, but statistically significant changes being made.

Figure 7:
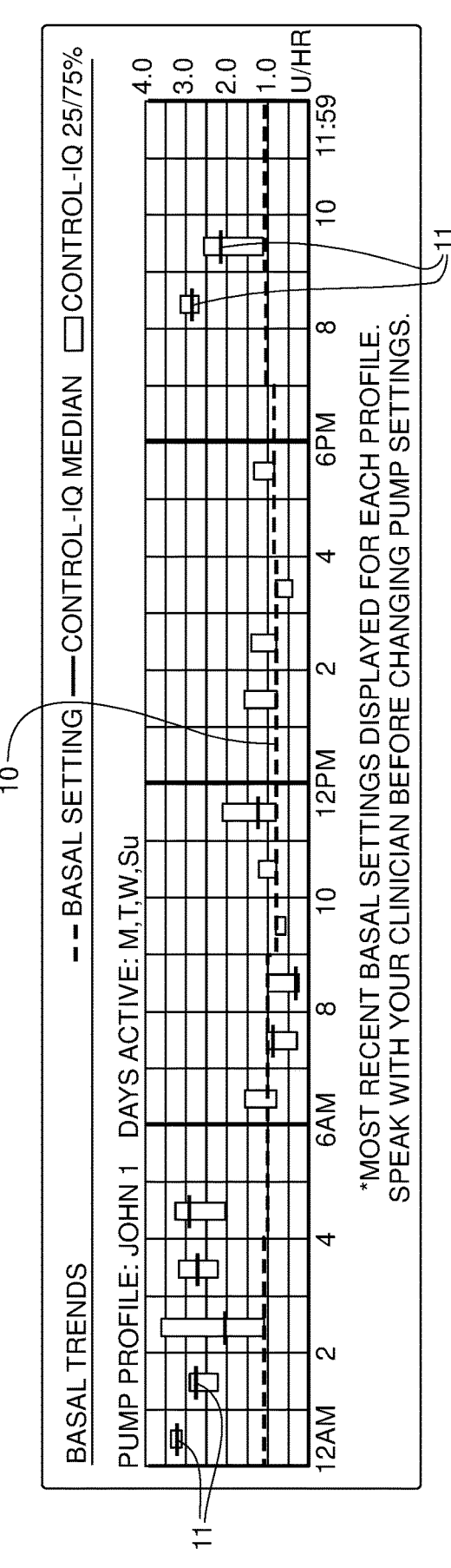
FIG. 7 depicts a basal trends chart for a user according to the disclosure.

Referring to FIG. 7, a graphical depiction of a user's basal profile overlain with actual insulin delivery based on a closed loop algorithm as described herein is displayed. In particular, the continuous line 10 represents the user's programmed basal profile and the discrete lines 11 represent a median delivery rate actually delivered by the pump based on the algorithm for a given time period of the day. For example, referring back to the basal profile described above, if the closed loop algorithm adds, on average, 0.1 u/hr to the overnight (12:00 AM to 6:30 AM) programmed rate of 1 u/hr, the graph will show a line at 1.1 u/hr above the programmed rate over that time period. The result is that two different profiles can be established and depicted in such a format—1) the user's pre-programmed basal profile and 2) the actual delivery profile as determined by the closed loop algorithm. The two profiles can be compared and, on the assumption that the actual insulin delivered represents the correct profile, if the difference between the profiles is statistically significant the programmed profile is determined to have the wrong shape and can be modified.

To compare continuous variables, such as basal rates, there is a technique called the Kolmogorov-Smirnov Test, or K-S Test. This test is used to compare two distributions statistically and returns a probability (p) used to assess similarity between the two distributions. If p is less that 0.05, the distributions are statistically different. In considering how to optimize a user's basal profile, the present disclosure can consider the basal profile to be a probability distribution because the higher the basal rates, the greater the probability of the user receiving a higher dose of insulin. By considering the basal profile as such, the K-S Test can further be advantageously employed to compare the cumulative probability distributions and identify the largest difference between the two. Thus, not only does use of the K-S test with basal rates in the described manner identify whether or not the stored profile and actual delivery are statistically different, it can also identify where the greatest difference occurs, which, in the case of a basal profile, means identifying the time period of the day where the greatest difference occurs. Therefore, if it is determined that the two distributions are different, the optimal modification to achieve further similarity is the time period where the greatest difference occurs as identified with the K-S Test.

The equation for the K-S test is based upon the maximum difference between the two cumulative distributions as shown in equation (1), with the x value at which D is selected being "Z".

$$D = \max_{-\infty < x < \infty} |S(x) - P(x)| \tag{1}$$

As applied to basal rates according to the present disclosure, P(x) in equation (1) is the user's programmed cumulative profiled basal rate and S(x) is the user's adjusted cumulative basal rate profile as actually delivered according to the closed loop algorithm. The equation to calculate the probability to determine if the difference D is statistically significant (i.e., if p<0.05 the two distributions are different) is presented in equation (2)

$$p = Q_{KS}\left(\left[\sqrt{N_e + 0.12 + \frac{0.11}{\sqrt{N_e}}}\right]D\right) \tag{2}$$

In equation (2), $N_e$ represents the effective number of data points, which in one embodiment for basal rates is 288 (calculated as 12 basal rates per hour—in the case of a closed loop delivery calculation every 5 minutes—times 24 hours). The variable $Q_{ks}$ is calculated as $1-P_{ks}$, with $P_{ks}$ being calculated at a given x value Z (i.e., time of day) according to equation (3).

$$p = Q_{KS}\left(\left[\sqrt{N_e} + 0.12 + \frac{0.11}{\sqrt{N_e}}\right]\right)D \tag{3}$$

Thus, with the above equations and the basal rate data for the patient, it can be determined whether or not the difference between the programmed basal profile and the actual basal delivery is statistically significant as well as the time of day Z when the profile should be modified.

Figure 8:
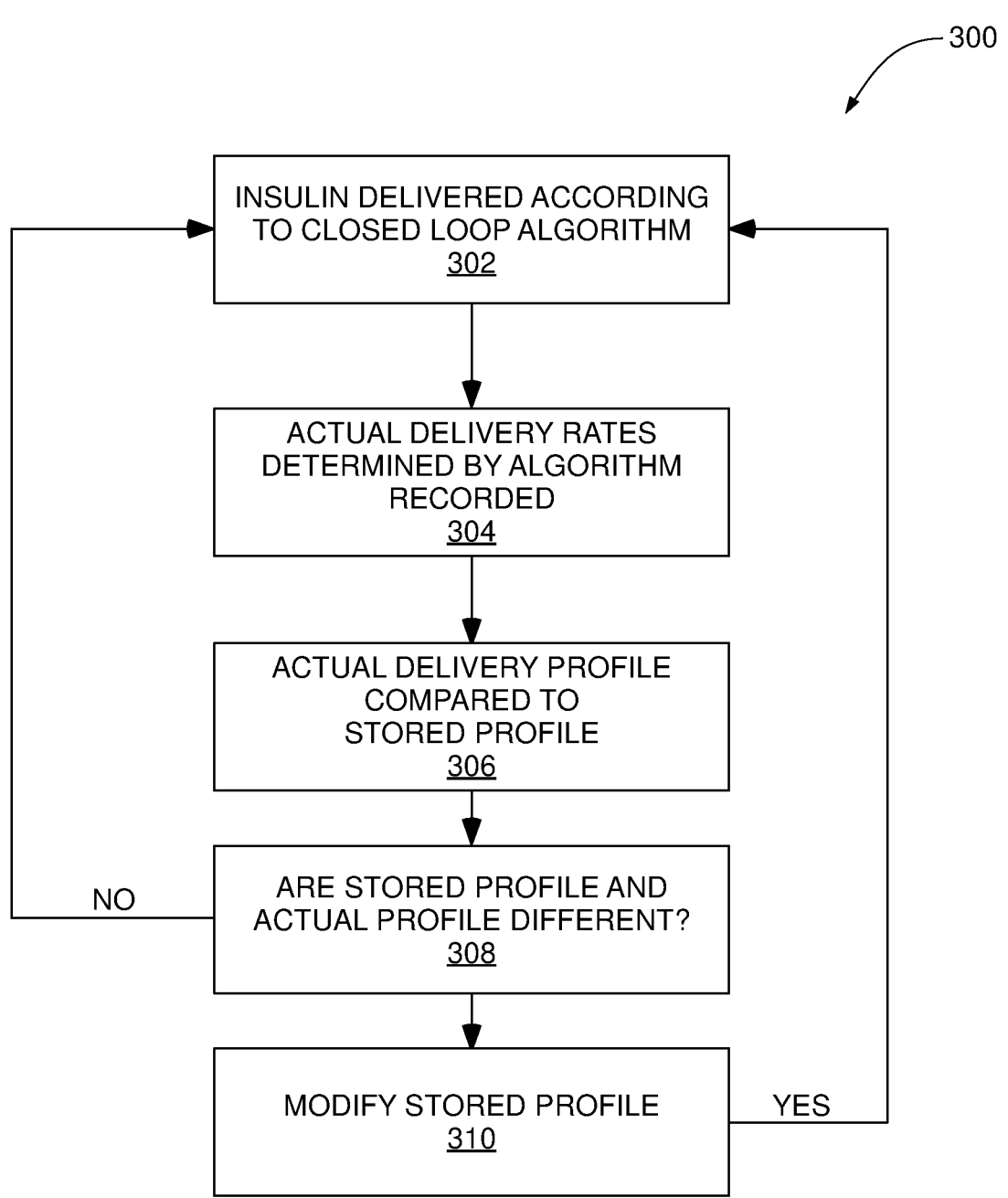
FIG. 8 depicts a flowchart of method steps for a method of modifying a user profile in automated insulin delivery according to an embodiment.

FIG. 8 depicts a flowchart of method steps for a method of modifying a user profile in automated insulin delivery 300 according to an embodiment. At step 302, insulin is delivered to the user with an infusion pump as calculated by a closed loop delivery algorithm. As noted above, such an algorithm may utilize a stored basal profile of the user as a baseline and modify delivery higher or lower than the baseline based on glucose levels of the user. As indicated at step 304, the delivery rates actually delivered to the user based on the closed loop algorithm are recorded as they are delivered. At step 306, the actual delivery rates are compared to the stored basal profile, such as, for example, by using the K-S Test as described herein. It is then determined from the comparison whether differences between the two profiles are statistically different based, for example, on the equations set forth above. If the profiles are not statistically different, the system can continue at step 302 delivering insulin according to the stored profile. If the profiles are statistically different, then the stored profile can be modified at step 310 at which point the system can begin delivering insulin according to the closed loop algorithm at step 302 using the modified stored profile. For example, the profile can be modified as set forth above by modifying the basal rate at the time of day for which the cumulative distributions differed the most.

In embodiments, the above-described comparison can be based on a predetermined time period and can occur on a regular or intermittent basis. For example, the comparison can be made for each basal rate employed over a 24 hour period for a predetermined number of days. In some embodiments, delivery can be tracked and the comparison made every 7 days based on average rates over the seven days for each time period.

In an embodiment, an ambulatory infusion pump system can include a pump mechanism configured to facilitate delivery of insulin to a user, a communications interface adapted to receive glucose levels from a continuous glucose monitor and at least one processor functionally linked to the pump mechanism and the communications device. The at least one processor can be configured to automatically calculate insulin doses with a closed loop delivery algorithm based on glucose levels received from the continuous glucose monitor with the closed loop delivery algorithm employing a default basal profile when the user's glucose levels are within a target glucose level range defining a default basal rate for a plurality of times of day. The closed loop delivery algorithm can be configured to increase or decrease insulin delivery from the default basal rate when the user's glucose levels are outside of the target glucose level range. The processor can further be configured to record actual insulin delivery rates delivered to the user based on the closed loop delivery algorithm for the plurality of times of day and conduct a comparison of the default basal profile with the actual insulin delivery rates to determine whether a difference between the actual insulin delivery rates and the default basal profile is statistically significant. If the difference between the actual insulin delivery rates and the default basal profile is statistically significant, the default basal profile can be modified.

In some embodiments, the default basal profile includes a plurality of different basal rate amounts to be delivered at different times of day.

In some embodiments, modifying the default basal profile includes modifying a subset of the different basal rate amounts.

In some embodiments, the at least one processor is configured to compare the default basal profile with the actual insulin delivery rates using the Kolmogorov-Smirnov Test.

In some embodiments, a result of the Kolgorov-Smirnov tests determines whether the difference between the actual insulin delivery rates and the default basal profile is statistically significant.

In some embodiments, a result of the Kolgorov-Smirnov tests determines a time of day when a greatest difference occurs between the actual insulin delivery rates and the default basal profile.

In some embodiments, the at least one processor is configured to modify the default basal profile at the time of day when a greatest difference occurs between the actual insulin delivery rates and the default basal profile.

In some embodiments, the at least one processor is configured to compare the default basal profile with the actual insulin delivery rates over a predetermined time period.

In an embodiment a method of diabetes therapy includes automatically calculating insulin doses with a closed loop delivery algorithm based on glucose levels received from the continuous glucose monitor. The closed loop delivery algorithm can employ a default basal profile when the user's glucose levels are within a target glucose level range, the default basal profile defining a default basal rate for a plurality of times of day and the closed loop delivery algorithm configured to increase or decrease insulin delivery from the default basal rate when a user's glucose levels are outside of the target glucose level range. Insulin can automatically be delivered to the user based on the calculated insulin doses. Actual insulin delivery rates delivered to the user based on the closed loop delivery algorithm can be recorded for the plurality of times of day. The default basal profile can be compared with the actual insulin delivery rates to determine whether a difference between the actual insulin delivery rates and the default basal profile is statistically significant. If the difference between the actual insulin delivery rates and the default basal profile is statistically significant, the default basal profile can be modified.

In some embodiments, the default basal profile includes a plurality of different basal rate amounts to be delivered at different times of day.

In some embodiments, modifying the default basal profile includes modifying a subset of the different basal rate amounts.

In some embodiments, comparing the default basal profile with the actual insulin delivery rates uses the Kolmogorov-Smirnov Test.

In some embodiments, determining whether the difference between the actual insulin delivery rates and the default basal profile is statistically significant utilizes a result of the Kolgorov-Smirnov tests.

In some embodiments, determining a time of day when a greatest difference occurs between the actual insulin delivery rates and the default basal profile utilizes a result of the Kolgorov-Smirnov tests.

In some embodiments, modifying the default basal profile includes modifying the default basal profile at the time of day when a greatest difference occurs between the actual insulin delivery rates and the default basal profile.

In some embodiments, comparing the default basal profile with the actual insulin delivery rates occurs over a predetermined time period.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357, 603; 10,357,606; 10,492,141; 10/541,987; 10,569,016; 10,736,037; 10,888,655; 10,994,077; 11,116,901; 11,224, 693; 11,291,763; 11,305,057; 11,458,246; and 11,464,908 and commonly owned U.S. Patent Publication Nos. 2009/ 0287180; 2012/0123230; 2013/0053816; 2014/0276423; 2014/0276569; 2014/0276570; 2018/0071454; 2019/ 0307952; 2020/0206420; 2020/0329433; 2020/0368430; 2020/0372995; 2021/0001044; 2021/0113766; 2021/ 0154405; 2021/0353857; 2022/0062553; 2022/0139522; 2022/0223250; 2022/0233772; 2022/0233773; 2022/ 0238201; 2022/0265927; and 2022/0344017 and commonly owned U.S. patent application Ser. Nos. 17/368,968; 17/732, 208; 17/878,681; 17/879,959; 17/886,998; 17/896,492; 17/961,206; and 17/964,513.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump system, comprising:
a pump mechanism configured to facilitate delivery of insulin to a user;
a communications interface adapted to receive glucose levels from a continuous glucose monitor;
at least one processor functionally linked to the pump mechanism and the communications interface, the at least one processor configured to:
automatically calculate insulin doses with a closed loop delivery algorithm based on glucose levels received from the continuous glucose monitor, the closed loop delivery algorithm employing a default basal profile when the user's glucose levels are within a target glucose level range, the default basal profile defining a default basal rate for a plurality of times of day and the closed loop delivery algorithm configured to increase or decrease insulin delivery from the default basal rate when the user's glucose levels are outside of the target glucose level range;
record actual insulin delivery rates delivered to the user based on the closed loop delivery algorithm for the plurality of times of day;
compare a first distribution of the default basal profile with a second distribution of the actual insulin delivery rates to determine whether a difference between the first and second distributions is statistically significant; and
modify the default basal profile if the difference between the first and second distributions is statistically significant.

2. The ambulatory infusion pump system of claim 1, wherein the default basal profile includes a plurality of different basal rate amounts to be delivered at different times of day.

3. The ambulatory infusion pump system of claim 2, wherein modifying the default basal profile includes modifying a subset of the different basal rate amounts.

4. The ambulatory infusion pump system of claim 1, wherein the at least one processor is configured to compare the first distribution of the default basal profile with the second distribution of the actual insulin delivery rates using the Kolmogorov-Smirnov Test.

5. The ambulatory infusion pump system of claim 4, wherein a result of the Kolmogorov-Smirnov test determines whether the difference between the first and second distributions is statistically significant.

6. The ambulatory infusion pump system of claim 4, wherein a result of the Kolmogorov-Smirnov test determines a time of day when a greatest difference occurs between the first and second distributions.

7. The ambulatory infusion pump system of claim 6, wherein the at least one processor is configured to modify the default basal profile at the time of day when the greatest difference occurs between the first and second distributions.

8. The ambulatory infusion pump system of claim 1, where the at least one processor is configured to compare the first distribution of the default basal profile with the second distribution of the actual insulin delivery rates over a predetermined time period.

9. A method of diabetes therapy, comprising:

automatically calculating insulin doses with a closed loop delivery algorithm based on glucose levels received from a continuous glucose monitor, the closed loop delivery algorithm employing a default basal profile when the glucose levels are within a target glucose level range, the default basal profile defining a default basal rate for a plurality of times of day and the closed loop delivery algorithm configured to increase or decrease insulin delivery from the default basal rate when the glucose levels are outside of the target glucose level range;

automatically delivering insulin to the user based on the calculated insulin doses;

recording actual insulin delivery rates delivered to the user based on the closed loop delivery algorithm for the plurality of times of day;

comparing a first distribution of the default basal profile with a second distribution of the actual insulin delivery rates to determine whether a difference between the first and second distributions is statistically significant,; and modifying the default basal profile if the difference between the first and second distributions is statistically significant.

10. The method of claim 9, wherein the default basal profile includes a plurality of different basal rate amounts to be delivered at different times of day.

11. The method of claim 10, wherein modifying the default basal profile includes modifying a subset of the different basal rate amounts.

12. The method of claim 9, wherein comparing the first distribution of the default basal profile with the second distribution of the actual insulin delivery rates uses the Kolmogorov-Smirnov Test.

13. The method of claim 12, wherein determining whether the difference between the first and second distributions is statistically significant utilizes a result of the Kolmogorov-Smirnov test.

14. The method of claim 12, further comprising determining a time of day when a greatest difference occurs between the first and second distributions utilizing a result of the Kolmogorov-Smirnov test.

15. The method of claim 14, wherein modifying the default basal profile includes modifying the default basal profile at the time of day when the greatest difference occurs between the first and second distributions.

16. The method of claim 9, where comparing the first distribution of the default basal profile with the second distribution of the actual insulin delivery rates occurs over a predetermined time period.

* * * * *